United States Patent [19]

Ayme et al.

[11] 4,242,270

[45] Dec. 30, 1980

[54] PROCESS FOR SEPARATING LIPIDS FROM ENDOTOXINS

[75] Inventors: Gerard Ayme, Lyon; Ladislas Szabo, Verrieres-le-Buisson, both of France

[73] Assignee: Institut Merieux, Lyons, France

[21] Appl. No.: 910,895

[22] Filed: May 30, 1978

[30] Foreign Application Priority Data

May 31, 1977 [FR] France ................................. 77 16473

[51] Int. Cl.$^3$ ........................... C11B 1/10; C09F 5/10
[52] U.S. Cl. .............................. 260/412.8; 260/236.5; 260/428.5; 424/92
[58] Field of Search ............. 424/92; 260/236.5, 412.8

[56] References Cited

U.S. PATENT DOCUMENTS

| | | | |
|---|---|---|---|
| 2,359,388 | 10/1944 | Roberts et al. | 424/92 |
| 2,371,002 | 3/1945 | Strean | 424/92 |
| 2,635,984 | 4/1953 | Eggert | 424/92 |
| 2,701,226 | 2/1955 | Pillemer | 424/92 |
| 2,965,543 | 12/1960 | Thiele | 424/92 |
| 3,089,821 | 5/1963 | Folkers | 424/92 |
| 3,148,120 | 9/1964 | Westphal | 424/92 |
| 3,185,624 | 5/1965 | Nakazawa | 424/92 |
| 3,395,219 | 7/1968 | Millman | 424/92 |
| 3,405,218 | 10/1968 | Haskell et al. | 424/92 |
| 3,438,862 | 4/1969 | Work | 424/92 |
| 3,465,078 | 9/1969 | Spiesel | 424/92 |
| 4,029,766 | 6/1977 | Helting | 424/92 |

OTHER PUBLICATIONS

Le Dur, A., Caroff, M., Chaby, R., Szabo, L., Eur. J. Biochem. 84(2): 579-590, (1978), A Novel Type of Endotoxin Structure Present in Bordetella Pertussis-Isolation of 2 Different Polysaccharides Bound to Lipid A.

Haeffner, N., Chaby, R., Szabo, L., Eur. J. Biochem. 77(3): 535-544, (1977), Identification of 2 Methyl-3-Hydroxy Decanoic Acid and 2 Methyl 3 Hydroxy Tetra Decanoic Acid in the Lipid X Fraction of Bordetella Pertussis Endotoxin.

Chem. Abst. 85 #175362b (1976), Klimanova Study on the Chemical Structure of O-Antigens with varying Toxicity from Bordetella Pertussis Prob. Usoversh. Akds-Vaktsiny 1975: 57-65.

Chem. Abst. 79 #24925 (1973), Thiele et al., Free Lipids of Brucella Melitensis And Bordetella Pertussis, Eur. J. Biochem. 1973, 34(2): 333-344.

*Primary Examiner*—John F. Niebling
*Attorney, Agent, or Firm*—Cushman, Darby & Cushman

[57] ABSTRACT

Bacterial endotoxins are hydrolyzed to yield lipid fractions which exhibit biological activity equal to, and in some instances greater than, the biological activity of the parent endotoxin.

11 Claims, 1 Drawing Figure

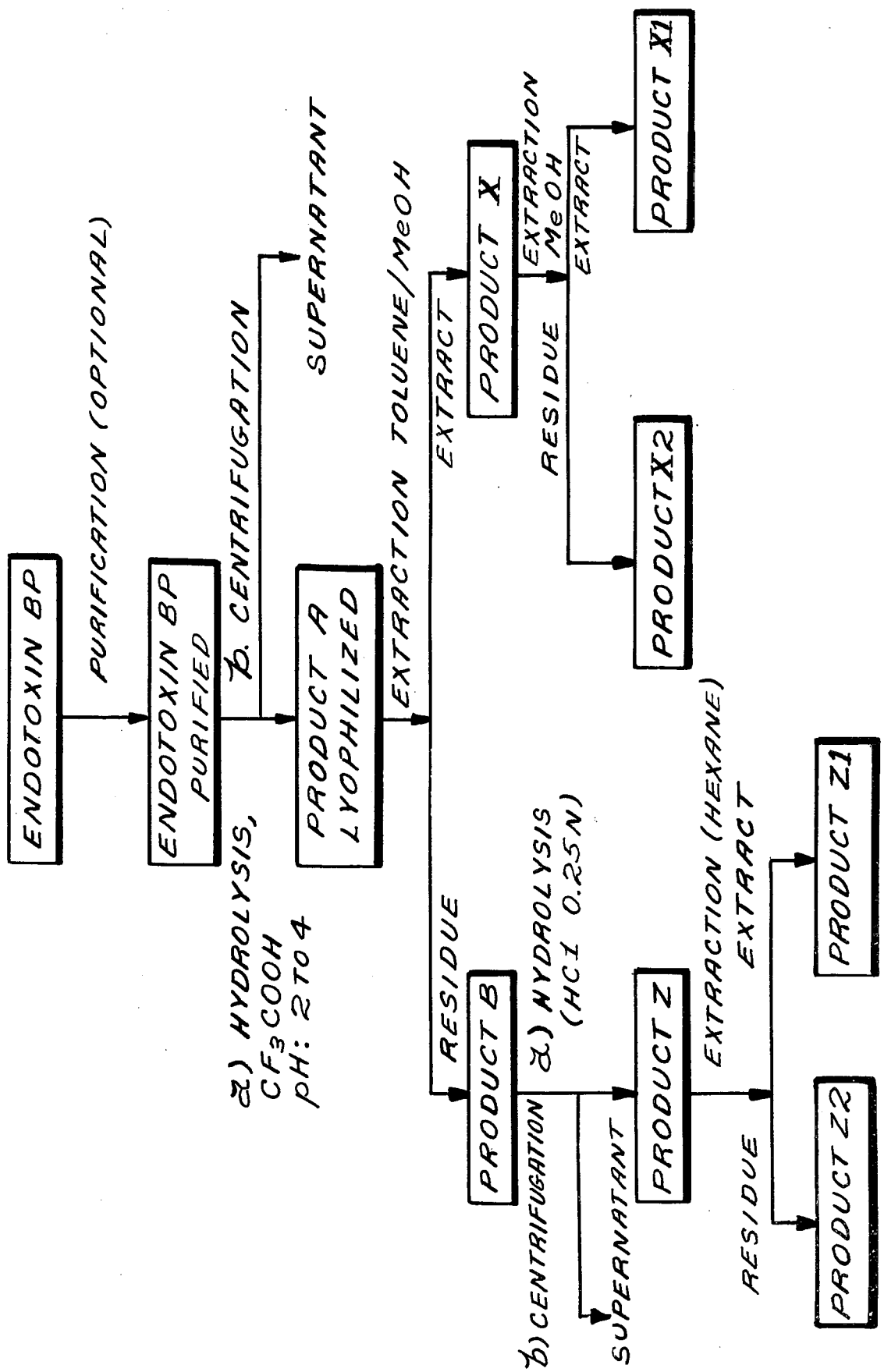

PROCESS FOR SEPARATING LIPIDS FROM ENDOTOXINS

The present invention is directed to a process of separating lipids from bacterial endotoxins, particularly the endotoxin Bordetella Pertussis, and to the various resulting lipid fractions and their use as pharmaceutical compositions.

The applicants' research confirms that the various resulting fractions, resulting from the process of the invention, exhibit different biological activities as adjuvants in non-specific immunity applications.

Further, it has been established that certain fractions are toxic and pyrogenic, while other fractions are not.

Through research involving the invention, it has been confirmed that the lipid fractions of endotoxin are responsible for the biological activity exhibited by gram-negative bacteria.

However, so far in the case of other gram-negative bacteria, the biological activities were attributed solely to the single macromolecule named Lipid A according to the terminology of O. Westphal.

The applicants have unexpectedly discovered that said biological activities are not uniquely localized in said macromolecule.

According to the present invention, it is possible to detoxify certain lipid fractions of the Bordetella Pertussis endotoxin, while retaining or increasing certain biological properties of the endotoxin, particularly its adjuvant activity.

Thus, such fractions can be used in the pharmaceutical field to reinforce the effect of viral and bacterial vaccines, to reinforce the defense system of the organism and to fight against certain bacterial infections (Salmonella, Pseudomonas, Staphylococci, Klebsiella), as well as viral infections (Semliki Forest virus, encephalomycarditis virus).

Furthermore, such fractions can be active against tumoral diseases (Erlich's ascitis, lymphoma YC8).

The process of the present invention results in the separation of various lipid fractions of bacterial endotoxins, and particularly Bordetella Pertussis endotoxin and comprises subjecting the endotoxin, which optionally has been purified, to mild hydrolysis with an organic acid, at a pH of from 2 to 4; separating the supernatant from the residue which has formed and lyophilizing said residue, the lyophilized product being referred to as product A.

Further process steps in accordance with the invention involve two separate extraction stages. In one stage, product A can be extracted with a first solvent to produce an extract (product X) and a residue (product B); said product X is capable of being extracted with a solvent which is different from said first solvent to result in a new extract (product X1) and a residue (product X2).

According to a second stage, other additional lipid fractions can be obtained by more thorough hydrolysis of said product B.

According to this second stage, product B is subjected to a hydrolysis with HCl at a pH equal to or less than 1. After elimination of the supernatant, the residue resulting from this hydrolysis is lyophilized (product Z) and, if desired, is then subjected to an extraction resulting, on the one hand, in an extract (product Z1) and on the other hand a residue (product Z2).

According to a preferred embodiment, product Z2 can be obtained in purified form by extraction with a solvent and elimination of the residue.

The various stages of the process include optionally purifying endotoxin BP and hydrolyzing the thus purified endotoxin. The hydrolysis product is then centrifuged, the supernatant being discarded and the residue is lyophilized to provide product A which is then extracted to provide product X and product B, the latter being the residue of this extraction. Product X is extracted to give product $X_1$ and product $X_2$, the latter being the residue of this extraction. Product B is hydrolyzed to give, after elimination of the supernatant following centrifugation, product Z. Product Z is then extracted to give product $Z_1$ and product $Z_2$, the latter being the residue of this extraction procedure.

The preparation and isolation of the Bordetella Pertussis Endotoxin is known and can be obtained by methods described in the literature and particularly in the following publications: *Biochem. J.*, 74 398–409 (1960); *Japan J. Microbiol.* 14, 1–8 (1970); and *Canad. J. Microbiol.* 19, 231–237 (1973).

The endotoxin can be purified by various known methods. According to the present invention purification of the endotoxin is optional. Purification can be effected by a series of extractions with various solvents, a first extraction with chloroform, then an extraction with a 1:1 mixture of toluene and methanol and finally an extraction with methanol. Such a purification makes it possible to eliminate between 1 to 2% of soluble materials.

As indicated above, the hydrolysis of the endotoxin is performed under mild conditions at a pH between 2 and 4, preferably at a pH of 2.4, with an organic acid, and preferably with trifluoroacetic acid, for about 50 to 150 hours and at a temperature of 40° to 60° C.

After centrifuging, the supernatant is eliminated and the residue is lyophilized to yield a product designated product A.

According to the first embodiment of the invention, product A is then subjected to an extraction with an organic solvent, preferably a mixture of solvents such as a toluene/methanol 1:1 mixture.

The residue resulting from the extraction constitutes product B and the remaining extraction mixture, after evaporation, leads to product X which is itself subjected to an extraction with methanol which leads to a residue (product X2), on the one hand, and, on the other hand, after evaporation of the extract to a product X1.

According to the second embodiment of the process, product B, as described above, is subjected to an acid hydrolysis with HCl at a pH equal to or less than 1 at a temperature around 100° C. for about 15 to 60 minutes.

After centrifuging the hydrolysis reaction mixture, the supernatant is discarded and the resulting residue optionally washed with 0.25 N HCl acid and with water is again centrifuged and is then lyophilized thus leading to product Z.

Product Z, after hexane extraction, yields, on the one hand, after evaporation, an extract (product Z1) and, on the other hand, a residue (product Z2). Product Z2, according to a further embodiment, can be obtained in purified form by extracting it, preferably with a mixture of solvents such as a toluene/methanol 1:1 mixture and by discarding any of the residue.

In the description which follows, all reference to product Z2 should be understood as referring to the purified form of product Z2.

Of course, the various stages leading to the various lipid fractions of Bordetella Pertussis endotoxin can be undertaken with certain modifications or variations without thereby deviating from the scope of the invention.

The principal and most important stage of the process is the mild hydrolysis of the endotoxin. As indicated above, the endotoxin may be optionally purified prior to hydrolysis.

A principal object of the present invention is a novel industrial product selected from the group consisting of the various fractions obtained by the process according to the invention and in particular the products A, B, X, X1, X2, Z, Z1 and Z2.

There will now be given by way of illustration an example in which separation of the various lipidic fractions of Bordetella Pertussis endotoxin is undertaken in accordance with the invention.

5.5 g of Bordetella Pertussis endotoxin (BP 35—strain 1414 phase I) are first subjected to a series of extractions for purification.

Firstly, the endotoxin is subjected to an extraction with 100 ml of chloroform; after removal of the solvent, the resulting residue is then subjected to an extraction with 2 100 ml portions of a toluene/methanol 1:1 mixture. As previously, the solvent is removed and the residue again subjected to an extraction by using 100 ml of methanol as solvent.

The resulting residue, 5.345 g, comprises the purified endotoxin. The foregoing series of extractions makes it possible to eliminate about 75 mg of soluble materials.

Then the endotoxin is placed in a suitable container and 1,360 ml of trifluoroacetic acid (pH of medium is 2.43) are added.

It is then heated at 50° C. for 115 hours.

After cooling, the reaction mixture is centrifuged in an MSE type MR 25 apparatus (3000 rpm, 20 minutes) and the supernatant, which is made up principally of polysaccharides, is discarded. The residue is then lyophilized to yield 3.422 g of product A.

Isolation of fractions X, X1 and X2 and fractions B, Z, Z1 and Z2

Product A (3.422 g) is subjected to an extraction with 4 100 ml portions of a toluene/methanol 1:1 mixture. After elimination of the solvent under reduced pressure, 226.8 mg of an extract (product X) are obtained; the extraction residue constitutes product B (3.180 g).

(i) Isolation of fractions X1 and X2.

226.8 mg of product X is extracted with 100 ml of methanol. The residue of extraction (107.2 mg) constitutes product X2. After evaporation of the solvent under reduced pressure, product X1 (100.2 mg) is isolated.

(ii) Isolation of fractions Z, Z1 and Z2.

The 3.180 g of product B obtained above are placed in a suitable container and subjected to a hydrolysis with 1,600 ml of 0.25 N hydrochloric acid at a temperature of 100° C. for 30 minutes.

After cooling, the hydrolysis mixture is centrifuged; and after elimination of the supernatant containing polysaccharide substances, the residue is optionally washed with 0.25 N HCl and water, and is centrifuged under the same conditions as above. The ultimate residue is then freeze dried to yield 1.23 g of product Z.

By extraction of product Z with 100 ml of hexane and elimination of the solvent under reduced pressure, product Z1 (50.45 mg) is obtained. The extraction residue is subjected to an extraction with 100 ml of a toluene/methanol 1:1 mixture and after elimination of the solvent under reduced pressure, 823 mg of product Z2 are obtained.

Biological study of the various fractions obtained

1. Pyrogenic power and toxicity

All mammals are sensitive to endotoxins, but the response depends on the mode of administration to the animal species, the dosage and the individual. With a small dose, the animal exhibits only slight response such as increase in temperature, a drop in weight; with a high dose, the endotoxins can cause extreme reactions such as the Schwartzmann phenomenon and even death of the animal.

(a) Pyrogenic effect

The pyrogenic effect of various fractions was tested for each product on three rabbits. The results are expressed as the sum of the temperature variations ($\Sigma \Delta t°$).

It should be noted that a product is considered as pyrogenic when its $\Sigma \Delta t° \geq 1.5°$ (Pharmacopee Europeenne—European Pharmacopoeia).

| Products dose: 2 $\mu$g ml$^{-1}$ kg$^{-1}$ administered intravenously | A | B | X | X1 | X2 | Z | Z1 | Z2 |
|---|---|---|---|---|---|---|---|---|
| $\Sigma \Delta t°$ | 5 | 6.65 | 5 | 2 | 4.3 | 1.2 | 0.75 | 1.1 |

These results show that product Z and the fractions resulting from it (products Z1 and Z2) are not pyrogenic or only slightly so while the other fractions are pyrogenic.

When the actual dosages are taken into consideration, the pyrogenic effect of fractions is very slight, if compared with a reference endotoxin of Escherichia coli which for a dose of 1 $\mu$g kg$^{-1}$ gives $\Sigma \Delta t° = 1.35°$.

(b) Mouse-Weight-Gain-Test (MWGT)

The MWGT consists in inoculating groups of rapidly growing mice (12-14 g) intraperitoneally with different doses of the products to be tested. A control group is inoculated with physiological saline solution. The mice are weighed individually on the day of injection (D0), then by group one day (D1), three days (D3) and seven days (D7) afterwards. For each of the dosages, the variation in weight in relation to the control group as a function of time is calculated for each product and the corresponding curves are plotted whose surfaces ($\Delta S$) are determined.

Then there is calculated in the dose $D_o$ of the product. $D_o$ corresponds to a zero $\Delta S$ and a dose which would not have involved disturbance of the weight curve of the group inoculated with the product in relation to the control group.

In the following table are given the dose ($D_o$) obtained for various products.

| Products | A | B | X | X1 | X2 | Z | Z1 | Z2 |
|---|---|---|---|---|---|---|---|---|
| $D_o$ $\mu$g/mouse | 6 | 21 | 61 | 183 | 48 | 58 | 58 | 69 |

The results show that products A and B are most toxic and that product X1 is least toxic.

(c) Schwartzmann Phenomenon

The Schwartzmann reaction is a hemorrhagic necrosis of certain organs observed after injection of a mammal (animal or man) with an endotoxin wherein the mammal is presensitized by a first injection of endotoxin from 6 to 48 hours before. The necrotic reaction can be cutaneously local if the first dose of endotoxin is injected in the skin and the second intravenously.

The reaction is generalized when the two injections are intravenous. The reaction can be obtained with two endotoxins without antigenic relationship.

In our study the first injection was made intravenously (injection of various fractions obtained from product A) and the second 17 hours later intravenously (this latter being made with a reference endotoxin).

The following table shows whether there was a necrotic reaction (+) or not (−).

| Products | A | B | X | X1 | X2 | Z | Z1 | Z2 |
|---|---|---|---|---|---|---|---|---|
| Necrotic reaction | +++ | +++ | + | − | + | − | − | − |

Analysis of these results indicates that there is a separation of the biological properties at the level of products X, X2 and products Z, Z2. Actually, products X, X2 are pyrogenic, and Schwartzmann positive, whereas products Z and Z2 are not pyrogenic, and do not exhibit a necrotic reaction in the Schwartzmann test.

2. Action on non-specific immunity

The various fractions obtained by the process of the invention were tested in the following way:

Mice with an average weight of 20 g receive intraperitoneally various doses of each product to be tested. After a wait of 3 days for bacterial tests and 1 day for viral tests, there is injected in the same way (except for the SF viral test where the injection is subcutaneous), a lethal dose of bacteria (I) or virus (II).

The results shown in the following table are expressed in % of surviving mice.

(I) Salmonella typhi ST.
*Pseudomanas aeruginosa* PA
(II) Encephalomyocarditis virus: BMC
"Semliki Forest" virus: SF

| Tests | Controls | Dose | A | B | X | X1 | X2 | Z | Z1 | Z2 |
|---|---|---|---|---|---|---|---|---|---|---|
| ST | DE : 0% | 1/1 | 90 | 90 | 90 | 40 | 100 | 80 | 40 | 70 |
|  | DE/5 : 10 | 1/4 | 30 | 60 | 20 | 0 | 40 | 20 | 0 | 30 |
|  | DE/25 : 80 | 1/16 | 10 | 0 | 10 | 0 | 0 | 30 | 0 | 0 |
| PA | DE : 0% |  | 90 | 70 | 60 | 0 | 60 | 0 | 0 | 10 |
|  | DE/5 : 20 |  | 0 | 20 | 10 | 0 | 10 | 0 | 0 | 0 |
|  | DE/25 : 90 |  | 0 | 0 | 0 | 0 | 0 | 0 | 0 | 0 |
| EMC | DE : 25% | 1/1 | 90 | 100 | 70 | 70 | 100 | 80 | 70 | 100 |
| SP | DE : 10 | 1/1 | 90 | 90 | 80 | 40 | 100 | 50 | 50 | 70 |

DE = Test dose

1/1, ¼ and 1/16: dilutions at a rate of four starting from the strongest dose 1/1: 200 μg per mouse.

The results obtained on the control mice show that the bacterial tests are more severe and thereby more significant than the viral tests. The mice that received the test doses died, whereas in the case of viral tests, a certain percentage of the test control mice lived.

These results show that the product X2 is capable of giving a total protection.

The results obtained indicate there are significant differences in the biological properties of the products X2 and Z2 and the results seem to confirm the separation of the biological properties observed for the pyrogenic and necrotic activity of fractions Z2 and X2.

3. Adjuvant Activity

The adjuvant activity can be measured through the effect of dosage on the increase of antibodies. Titration of the antibodies in the present case was performed by the passive hemagglutination technique; the strength of the antibodies is expressed as the inverse of the extreme dilution at which a positive reaction is still observed. For the various products the increase of antibodies was measured in response to the injection of an influenza vaccine (vaccine A and B) in mice. The minimal vaccine dose was measured for which there is obtained a response of specific antibodies of the influenza virus detectable in the passive hemagglutination technique. This measurement serves as a control. Then the mice are injected with this minimal dose (control) of vaccine (A or B) as well as the product it is desired to test. The two products, vaccine+adjuvant are mixed in a syringe and thus injected at the same time. 21 days after injection, the rate of antibody formation is determined.

The results are expressed as the inverse of the extreme dilution. The injection doses of the various fractions were 200 μg per mouse.

|  | Strength | |
|---|---|---|
| Mice inoculated with | Vaccine A | Vaccine B |
| Physiological salt solution | <20 | <20 |
| Antigen only | 201 | 101 |
| A | 806 | 320 |
| B | 506 | 400 |
| X | 1613 | 640 |
| X1 | 1280 | 160 |
| X2 | 806 | 506 |
| Z | 806 | 201 |
| Z1 | 806 | 400 |
| Z2 | 806 | 201 |

For the influenza vaccine, both vaccines A and B, the results indicate that of the lipidic products the products X and X1 have the highest adjuvant activity, even greater than that of the endotoxin. Products Z, Z1 and Z2 have the same adjuvant activity as the endotoxin but as indicated above, these products are not toxic or slightly toxic.

For vaccine B the adjuvant activity of the various products is slighter. However, the products X and X2 have the strongest adjuvant activity.

4. Action on tumors

The various fractions obtained according to the process of the invention were tested in the following way:

Mice of weight 16-18 g receive intraperitoneally 400 μg of each product to be tested; 4 hours later they are injected in the same way with $10^3$ tumor cells of Ehrlich's ascites (BA) or lymphoma YC8.

The animals are observed for two months at the end of which the survivors are noted.

The results are expressed in average survival time.

| Tumors | Controls | A | B | X | X1 | X2 | Z | Z1 | Z2 |
|---|---|---|---|---|---|---|---|---|---|
| BA | 21 days | >65 | 61 | 60 | >65 | >65 | >65 | >65 | >65 |
| YC8 | 26 days | 35 | 27 | 40 | 62 | 33 | 55 | 49 | 28 |

The results indicate that there is an activity of the products against the development of tumors.

In conclusion the products X, X1 or X2 are pyrogenic, Schwartzmann positive (except product X1), have a very high adjuvant power and give mice a non-specific immunity. Whereas the products Z, Z1 and Z2 are not pyrogenic, are Schwartzmann negative, retain the adjuvant activity of the starting product and have a very slight action on the non-specific immunity.

The invention is also directed to medicinal compositions based on the products obtained according to the process described above.

Taking into account the adjuvant activity of the various products as described above, the various products can be used in vaccines to reinforce the effect of the vaccines. Preferably, the fractions having the greater adjuvant power, and particularly products X, X1 and X2 will be used.

However, the products A, B, Z, Z1 and Z2 can also be used, although their adjuvant power is lower, because some of these products and particularly products X, Z1 and Z2 are not pyrogenic and only slightly toxic.

The exact doses of the adjuvant products produced in accordance with the invention will depend on the mammal species (specific animal or human), or on the vaccine per se, the antigen dose for each vaccine being an amount effective and sufficient to obtain, in the species considered, a satisfactory immunity level.

On the other hand, the remarkable qualities of stimulation of the immunity functions in regard to bacterial or viral infections and tumor processes permits the use of products X and X2, as well as A and B as immunostimulant medicine.

What is claimed is:

1. A process for separating the lipid fractions constituting a bacterial endotoxin such as Bordetella Pertussis endotoxin, comprising
   (a) under mild conditions, hydrolyzing the endotoxin with an organic acid at a pH of from 2 to 4 to produce a mixture of a supernatant and a residue;
   (b) separating the supernatant from the residue and lyophilizing the residue to yield a product denoted as product A;
   (c) extracting product A with 1:1 toluene/methanol mixture which results in a supernatant containing an extract denoted as product X and an insoluble residue denoted as product B; and
   (d) then extracting product X with a solvent different from the solvent mixture used in step (c) which results in a supernatant and an insoluble residue, wherein said residue is denoted as product $X_2$ and wherein the supernatant of step (d) contains an extract denoted as product $X_1$.

2. The process of claim 1, wherein said organic acid is trifluoroacetic acid.

3. The process of claim 1 wherein step (a) is undertaken at a temperature between 40° to 60° C. for about 50 to 150 hours.

4. The process of claim 1, wherein the solvent used in step (d) is methanol.

5. The process of claim 1, including step (e) wherein product B is hydrolyzed in hydrochloric acid at a pH up to 1 to produce a hydrolysis reaction mixture containing a residue; wherein the residue of step (e) is lyophilized to yield a product designated as product Z.

6. The process of claim 5, wherein step (e) hydrolysis is undertaken at a temperature of about 100° C. for about 30 minutes.

7. The process of claim 5, which further includes step (f) wherein product Z is extracted with hexane to yield a supernatant and an insoluble residue wherein the insoluble residue of step (f) is designated as product Z2 and wherein the supernatant of step (f) contains an extract designated as product Z1.

8. The process of claim 7, wherein product Z2 is purified by extracting it with toluene/methanol 1:1 mixture.

9. A product produced in accordance with claim 7 and selected from the group consisting of products A, B, X, X1, X2, Z, Z1 and Z2.

10. A product of claim 9 having a high adjuvant activity and, upon administration to mice, exhibiting a non-specific immunological activity, selected from the group consisting of products X, X1 and X2.

11. A product of claim 9 which exhibits an adjuvant activity equal to that of said endotoxin, selected from the group consisting of products Z, Z1 and Z2.

* * * * *